(12) United States Patent
Brunner et al.

(10) Patent No.: US 6,933,139 B2
(45) Date of Patent: Aug. 23, 2005

(54) METHOD FOR ENZYMATIC SPLITTING OF OILS AND FATS

(75) Inventors: Karlheinz Brunner, Grosskrotzenburg (DE); Rainer Frische, Frankfurt (DE); Dirk Kilian, Maintal (DE)

(73) Assignee: T+T Oleochemie GmbH, Alzenau (DE)

( * ) Notice: Subject to any disclaimer, the term of this patent is extended or adjusted under 35 U.S.C. 154(b) by 262 days.

(21) Appl. No.: 10/170,608

(22) Filed: Jun. 11, 2002

(65) Prior Publication Data

US 2002/0197687 A1 Dec. 26, 2002

(30) Foreign Application Priority Data

Jun. 21, 2001 (EP) .............................................. 01115081

(51) Int. Cl.$^7$ ................................................. C12P 7/64
(52) U.S. Cl. ...................................... 435/134; 435/198
(58) Field of Search .................................. 435/134, 198

(56) References Cited

U.S. PATENT DOCUMENTS

| | | | | |
|---|---|---|---|---|
| 4,026,462 A | * | 5/1977 | Tenthoff et al. | ................ 494/70 |
| 4,035,402 A | * | 7/1977 | Levine | ........................ 554/200 |
| 5,219,733 A | | 6/1993 | Myojo et al. | .................. 435/52 |

FOREIGN PATENT DOCUMENTS

| | | | | |
|---|---|---|---|---|
| DE | 19922882 A | 11/2000 | ............. | C12P/7/40 |
| EP | 0 195 311 A | 9/1986 | ............. | C11C/3/00 |

OTHER PUBLICATIONS

Rehm et al., Biotechnology, vol. 2, pp. 470–472, 1985, VCH.*

Continuous use of lipases in fat hydrolysis Buehler et al., Proc.—World Conf. Biotechnol. Fats Oils Ind. (1988), Meeting Date 1987, pp. 230–237.*

M. Bühler et al., "Enzymatische Fettspaltung", *Fat Science Technology*, Bd. 89, Nr. 4, (1987).

M. Bühler et al, "Oleochemicals by Biochemicals Reactions?", *Fat Science Technology*, Bd. 94, Nr. 3 (1992).

M. Bühler et al, "Continuous Use Of Lipases in Fat Hydrolysis", *Fat Science Technology*, Bd 89, Nr. 14 (1987).

T. Masanobu et al., "Hydrolysis Of Soybean Oil By Lipase With A Bioreactor Having Two Different Membranes", *Journal Of Fermentation And Bioengineering*, Bd. 75, Nr. 1, pp 53–57 (1993) (Abstract).

Gan Q et al., "Simultaneous Reaction And Separation in Enzymatic Hydrolysis Of High Oleate Sunflower Oil—Evaluation Of Ultrafiltration Performace And Process Synergy", *Chemical Engineering Journal*, Bd. 71, Nr. 2, pp. 87–96 (Dec. 2, 1998) (Abstract).

Patent Abstracts Of Japan, vol. 013, No. 111 (C–577), Mar. 16, 1989 & JP 63 287492 A (KAO Corp), Nov. 24, 1988.

* cited by examiner

*Primary Examiner*—Irene Marx
(74) *Attorney, Agent, or Firm*—Quarles & Brady LLP

(57) ABSTRACT

Method for the enzymatic splitting of oils and fats for obtaining fatty acids and glycerol by using lipases being added to a mixture containing an oil or fat and water, wherein the splitting reaction is performed only up to a splitting degree at which slowing-down of the splitting reaction is still below a preset value using discontinuously operated loop reactors, wherein the fatty acids to be obtained are separated from the reaction mixture that is only partially split, by first separating an aqueous glycerol-containing phase from a partially split organic phase containing split fatty acids, in a self-cleaning centrifugal separator and, afterwards, the fatty acids are separated from the partially split organic phase and the residue of the organic phase freed from the free fatty acids is fed back into the splitting process.

12 Claims, 6 Drawing Sheets

FIG. 1

FIG. 5, operation of the 2nd fat splitting stage with recovered enzyme

FIG. 6, recycling of the oil residue back to the splitting stage

METHOD FOR ENZYMATIC SPLITTING OF OILS AND FATS

CROSS-REFERENCE TO RELATED APPLICATIONS

This application claims the priority benefit of European patent application EP 01 115 081.0 filed on Jun. 21, 2001.

STATEMENT REGARDING FEDERALLY SPONSORED RESEARCH

Not Applicable.

FIELD OF INVENTION

The present invention relates to the enzymatic splitting or cleavage of native oils and fats, i.e. of the triglycerides of oils and fats, in the presence of water into glycerol and fatty acids.

BACKGROUND

Enzymatic splitting of fat or oil has been known for a long time and offers, contrary to a pressure splitting mainly practised in the industry, considerable principle advantages. The enzymatic splitting can be performed at normal pressure and, depending on the enzyme and oil or fat, even at room temperature.

It has also been known for a long time that this method of fat splitting is the most gentle one. The technical progress in industrial biotechnology also provided enzymes that are available now and suitable for fat splitting. Such available enzymes are e.g. used in numerous detergents. However, mainly because of the high enzyme consumption, of the very long splitting times and the resulting low efficiency of the enzymatic fat splitting, the enzymatic splitting did not become an industrial alternative method to the large-scale pressure splitting which is well established in industry.

The main problem that occurred in most of the numerous attempts to lower the enzyme consumption is described in the following publications: "Continuous Use of Lipases in Fat Hydrolysis", M. Bühler and Chr. Wandrey, Fat Science Technology 89/Dec. 87, pages 598 to 605; "Enzymatische Fettspaltung", M. Bühler and Chr. Wandrey, Fat Science Technology 89/Nr.4/1987, pages 156 to 164; and "Oleochemicals by Biochemical Reactions?", M. Bühler and Chr. Wandrey, Fat Science Technology 94/No. 3/1992, pages 82 to 94.

The enzymatic fat splitting using enzymes, so-called lipases, as biocatalysts acting on a water/oil mixture is described in these publications. By means of this splitting technique, the oil or fat, respectively, is split into glycerol and free fatty acids. The glycerol migrates into the water phase whereas the organic phase enriches more and more with free fatty acids until, finally, only the free fatty acids remain in the organic phase.

The activity of the used-up enzyme decreases to a great extent with time, and the decrease is mostly independent from the amount of the catalytically converted product. This reduction can be compensated by further additions of enzyme, however, a time-dependently varying enzyme consumption cannot be avoided. In the course of the splitting reaction, the reaction speed or splitting rate decreases more and more, and the enzyme consumption increases. This is due to the fact that the enzymatically catalysed hydrolysis is an equilibrium reaction. With an increasing concentration of glycerol in the water phase and of fatty acid in the organic phase, the reaction speed is slowed down and finally asymptotically approaches the equilibrium concentration. A desired splitting degree near 100%, therefore, can only be achieved after a very long reaction time. This long reaction time unavoidably results in a high loss of enzyme activity. The reaction time can be shortened by lowering the glycerol concentration in the water phase, this, however, implies a low concentration of the glycerol obtainable in the splitting reaction and, due to the higher percentage of the water phase, the water/gylcerine phase has more enzyme dissolved therein that will be discharged with the water phase and cannot be used again.

The enzymatic splitting reaction takes place at the phase boundary between organic and aqueous phase, and only enzyme being present at the phase boundary and triglycerides being present at the phase boundary contribute to or participate in the splitting reaction. With increasing splitting degree, the occupation density or concentration of fatty acids still chemically bonded as glycerides, in comparison to free fatty acids, decreases at the phase boundary so that the reaction is slowed down.

The reaction speed can be accelerated by increasing the interface boundary surface. However, this requires to increase the enzyme amount such that the occupation density or concentration of the enzyme at the phase boundary remains unchanged. The effect of increasing the reaction speed by addition of enzyme is, however, limited. At a maximum concentration, any further addition of enzyme does not contribute to accelerate the reaction. The enzyme consumption is, however, noticeably increased thereby, so that an optimal adjustment of the enzyme quantity and of the surface area of the phase boundary cannot be readily obtained.

Moreover, during a separation step for separating the organic, fatty acid containing phase and the glycerol containing water phase enzyme amounts are discharged and cannot be recovered for further use. It is true that the reaction speed can be increased by increasing the interface boundary surface by intensively mixing the organic and aqueous phase as well as the added enzyme amount, but phase separation, recovery and re-usage of the enzyme become more difficult thereby.

In the above mentioned publications, the enzymatic splitting reaction takes place in a continuous multistage counterflow system of water and oil which is to be subjected to splitting. When separating the aqueous phase containing glycerol and the organic phase containing the split free fatty acids, an intermediate or interfacial layer is generated. This interfacial layer is emulsion-like and contains most of the enzyme. In order to recover this enzyme for the process and to reduce the enzyme consumption, the process according to the aforementioned publication "Continuous Use of Lipases in Fat Hydrolysis" is conducted as follows: first, oil is continuously split in a mixing reactor. The reaction product which, besides free fatty acids, contains water, glycerol, mono- and diglyceride, not yet split oil as well as enzyme, is given into a solid wall bowl centrifuge. The centrifuge is adjusted such that the interfacial layer between the aqueous glycerol phase and organic phase is discharged together with the organic phase.

The organic phase containing the interfacial layer is fed into a second mixing reactor that is supplied with a fresh water/enzyme mixture. The reaction product of the second reactor is fed into a further solid wall bowl centrifuge that is, however, adjusted in such a manner that the interfacial layer is discharged together with the aqueous phase containing glycerol and such that the discharged free fatty acids are free of the interfacial emulsion layer. The aqueous phase is recycled into the first reactor (mixer), so that the enzyme amounts contained in the interfacial emulsion layer are again supplied or back-added to the process. The splitting degree achieved in the second reactor is up to 98%, so that the yield of free fatty acids after distillation of the end reaction product obtained form the second reactor is considerably high. However, even this kind of reaction scheme does not provide a process being actually competitive vis-a-vis the established large-scale pressure splitting process.

BRIEF SUMMARY OF THE INVENTION

The present invention provides a method for the enzymatic splitting of oils and fats for obtaining fatty acids and glycerol by using lipases being added to a mixture containing an oil or fat and water, wherein the splitting reaction is performed only up to a splitting degree at which slowing-down of the splitting reaction is still below a preset value using discontinuously operated loop reactors, wherein the fatty acids to be obtained are separated from the reaction mixture that is only partially split, by first separating an aqueous glycerol-containing phase from a partially split organic phase containing split fatty acids, in a self-cleaning centrifugal separator and, afterwards, the fatty acids are separated from the partially split organic phase and the residue of the organic phase freed from the free fatty acids is fed back into the splitting process.

A general objective of the present invention is to provide an enzymatic oil or fat splitting method which allows for a profitable competitive large-scale process.

This objective is achieved by means of the features of each one of the independent claims. Advantageous further embodiments are defined in the sub-claims. The inventive features provide a short reaction time and a reduced enzyme consumption.

These and still other objectives and advantages of the present invention will be apparent from the description which follows. In the detailed description below, preferred embodiments of the invention will be described in reference to the accompanying drawings. These embodiments do not represent the full scope of the invention. Rather the invention may be employed in other embodiments. Reference should therefore be made to the claims herein for interpreting the breadth of the invention.

DETAILED DESCRIPTION OF THE INVENTION

During their numerous attempts for finding solutions of the above object, the inventors of the present application evaluated that it was necessary to depart from the process scheme shown in the above mentioned publications in several basic and essential aspects. According to a first solution aspect of the present invention, the inventors departed from obtaining the desired yield of free fatty acids already with the enzymatic splitting as such which conventionally was conducted up to a high splitting or conversion degree. Instead, the enzymatic splitting according to this aspect of the present invention is only run up to or conducted until reaching a comparatively small splitting degree which corresponds to a splitting degree at which no considerable slow-down of the process occurs. In other words, the splitting reaction is stopped when the reaction rate falls below a preset value. Such a splitting degree normally lies between about 80% up to 90% and consequently below the splitting degree values that were hitherto considered necessary for a commercially applicable process.

Free fatty acids are then separated from the organic phase freed from enzyme, and the residue which still contains fatty acids chemically bonded as glycerides is fed back or recycled and mixed with fresh oil or fat to be subjected to splitting. In this manner, recycled glycerides are then subjected to a further enzymatic splitting process. If the enzymatic fat or oil splitting is run up to only a splitting degree of about 80%, this is possible in a very short time. If afterwards the free fatty acids are extracted from an oil or fat partially split in such a manner and if the chemically bound fatty acids (triglycerides) are returned or fed back into the splitting process, the enzyme consumption can be drastically reduced, without having to renounce to a final complete splitting of the oil or fat. The enzymatic splitting process does not get into the above mentioned critical process conditions in which the reaction speed, due to lack of glycerides at the phase boundary between aqueous and organic phase, is remarkably slowed down.

The splitting degree is determined as the ratio of the measured acid value divided by the theoretically possible acid value which can be computed for a given oil or fat. Preferably, the acid value is measured by means of titration according to standard common methods. Alternatively, the density of the aqueous glycerol phase can be taken as a measure for the splitting degree.

In order to separate the free fatty acids from the partially split starting product of the enzymatic splitting, preferably a vacuum distillation method is applied, that is, preferably a mild short path distillation (sometimes called molecular destillation). In the case of fats and oils with a chain length spectrum of the fatty acids of C14 to C22, as it holds true for most natural fats and oils, the free fatty acids can be separated by distillation without problems from the partially split starting product, i.e., fat or oil, and can be removed without concurrently distilling off any relevant quantities of glycerides or, in other words, any relevant quantities of fatty acids still chemically bonded as glycerides. In the case of splitting degrees between about 80 and 90%, the amounts of fatty acids chemically bonded as mono- and diglycerides are surprisingly small. The main part consists of the not yet split triglycerides. Moreover, quantities of free fatty acids remaining in the residue of the distillation step do not lead to a loss, since the residue is recycled into the splitting reaction. In one alternative to applying a distillation, the free fatty acids could be separated by an adsorptive separation method (e.g. column chromatography).

Advantageously, for distillation of the free fatty acids by means of vacuum distillation, vacuum-thin film-evaporators, such as falling-film or down-flow evaporators or short path distillation apparatus are used, since these distillation techniques, if compared to the bubble distillation technologies, are more gentle and, above all, can be continuously run. Moreover, these distillations techniques inherently require a liquid residue of about 5% to 10%, since otherwise the distillation film would tear off or break. Therefore, it constitutes a considerable advantage when, according to the invention, a reaction product still exhibiting a relatively small splitting degree is supplied to the vacuum distillation apparatus. Before recycling the bottom leaving the distillation apparatus, waxes or other undesired substances and by-products are separated, preferably by chemical-physical known measures, such as dewaxing, winterisation and bleaching. Otherwise, these substances would be enriched in the recycling process.

By means of the aforementioned measures, the reaction time could be drastically shortened in comparison to a process in which the enzymatic splitting as such was conducted so as to reach a splitting or conversion degree of 98% solely by continuous splitting. This was proved e.g. for High-Oleic sunflower oil. Moreover, the inventive comparatively early break-off of the enzymatic splitting strongly reduced enzyme losses due to the above mentioned decrease of enzyme activity with lapse of time. In comparison to working up to a splitting degree of 98% or the like, these losses can be remarkably reduced because the splitting reaction is stopped before the enzyme activity remarkably decreases. Accordingly, the process is such that the enzymatic fat splitting can be implemented with less costs than the pressure splitting. Consequently, the process according to the first aspect of the invention offers, for the first time, the possibility to use the enzymatic splitting as an advantageous alternative to the established industrial pressure splitting.

According to a further second solution aspect of the invention, the process time and the enzyme consumption can be considerably improved by using a self-cleaning centrifugal separator, a so-called separator with self-discharge, for separation of the heavier aqueous phase containing glycerol and the lighter organic phase containing fatty acids. The centrifugal separator is adjusted such that neither the organic phase nor the aqueous phase contain relevant amounts of the above mentioned interfacial emulsion phase which constitutes an emulsion phase being generated at the phase boundary or interface between the separated aqueous and organic phase and which contains substantial amounts of enzyme. The centrifugal separator is adjusted such that this interfacial emulsion phase accumulates in the separation zone inside the separator bowl, preferably lying in the area of the disk stack of the separator. The disk stack can be any disk-, rip- or wing-like structure lying within the separation zone of the self-cleaning centrifugal separator and being suitable for accumulating said emulsion phase.

The adjustment is achieved by known measures such as selecting and adjusting the ring dam diameter of the separator and the back pressure of the discharge pipes. An adequate adjustment is achieved when both phases, the aqueous phase and the organic phase, are discharged clear and emulsion-free. As common, both phases flow off during operation of the separator and can be observed.

This principally represents an unusual adjustment for a centrifugal separator, as in case of self-cleaning centrifugal separators, one normally avoids that considerable quantities of an intermediate or interfacial layer accumulate in the disk stack of the separator during a liquid/liquid phase separation. Instead, one generally takes care that any intermediate layer between the liquids to be separated is as small as possible and that the layer is discharged together with the phase that is not the phase to be primarily produced and does not accumulate in the separator. Principally, this also holds true for the system of the aforementioned publication, in which the intermediate or interfacial emulsion layer was discharged together with the aqueous phase behind the second, continuously operated solid-wall bowl centrifuge and was then fed back to the first mixing reactor.

The emulsion-like intermediate or interfacial layer is, according to the invention, accumulated in the centrifugal separator and discontinuously discharged by means of periodical discharges of the separator bowl, and the discharged accumulated intermediate layer containing the enzyme is re-used. It is recommendable to effect these periodic bowl discharges whenever the continuously discharged and flowing off organic phase and aqueous glycerol phase start to show any emulsion or clouding due to a concurrently discharged amount of the intermediate layer. The fact that with this intermittent bowl discharge, also aqueous phase and organic phase are completely discharged is not disadvantageous, since all phases are recycled into the splitting process.

In this manner, a discharge of any relevant enzyme amounts together with the heavy, aqueous phase or together with the light, organic fatty acid phase, is avoided so that, in effect, practically no considerable enzyme amounts are lost. The major portion of the enzyme accumulates in the disk stack of the separator and can be recovered and re-used by discontinuously full or partial bowl discharge. Instead of full bowl discharges, partial bowl discharges may also be applied, however, they should be adjusted such that the intermediate layer is as completely discharged as possible.

According to this aspect of the invention, enzyme losses due to discharge together with the aqueous phase and organic phase can be drastically lowered. In comparison to the time-dependent enzyme consumption due to unavoidable enzyme ageing, the discharge losses in the inventional process are very small.

A further development of the invention for achieving an even lower enzyme loss in the separated organic phase consists in using an additional self-cleaning polishing or clarifying centrifugal separator. This additional polishing separator is provided directly behind the separator of a single splitting stage or behind the final separator of a plurality of splitting stages and receives the organic phase discharged therefrom. Preferably, the additional polishing separator is provided in form of a self-cleaning centrifugal separator with disk stack. This separator is adjusted such that the sedimented solids, i.e., the enzymes in the present case, and the separable rest of the aqueous phase deposit at the bowl wall. The enzyme amounts centrifugally separated and deposited in this way are again obtained by discontinuous bowl discharge and recycled into the splitting-process.

By using a self-cleaning centrifugal separator for separation of the organic phase, the invention particularly offers the possibility of discontinuously conducting the splitting process in loop reactors or, in other words batch-wise. This is in contrast to the systems described in the above mentioned publications. For the purpose of the discontinuous process the following process can be adopted according to a third aspect of the invention: Oil is filled into a first loop reactor and the circulation loop of this reactor for circulating the reactor contents of oil (or fat), water and enzyme is not active at that time. At the same time, a second loop reactor conducts a splitting reaction with an active recirculation loop and a third loop reactor is discharged by means of a self-cleaning centrifugal separator during that time, whereby, by means of the centrifugal process in the separator, the discharged reaction mixture is separated into a glycerol containing aqueous phase, a fatty acids containing organic phase and an enzyme containing interfacial emulsion phase that constitutes the above intermediate layer. The latter one is discontinuously discharged in intervals from the separator, is supplemented with fresh enzyme and is returned into the reactor.

The splitting reaction can be conducted at a very high enzyme level, since the circulation as such and the shear forces being generated in the circulation pumps which are used to operate the circulation loop reactor produce an extraordinarily great interface boundary surface. Moreover when, according to the first aspect of the present invention, only 80% to 90% splitting degree are to be reached, the supplied water amount can be considerably reduced and it is possible to obtain an aqueous phase with highly increased glycerol concentration, which was not possible before. The reaction time is not remarkably lengthened even with glycerol concentrations above 30%. Such high glycerol concentrations have hitherto not been practicable. Moreover, a separation of the enzyme intermediate layer is promoted by the high glycerol concentration.

The operating mode according to the above third aspect of the present invention already allowed, in contrast to the above mentioned prior art, to reach in a short time frame of only one hour a splitting degree of up to 93%. At this degree a single-stage short path distillation can be carried out without problems according to the first aspect of the present invention. In case of a splitting degree of 95% or more, this would however, be rather difficult because of the reasons already mentioned.

As, according to the first aspect of the invention, the residue of the distillation is recycled into the splitting process, the material is completely converted without having to provide, as otherwise usual, a plurality of successive distillation stages or other separation means for separating the fatty acids.

The discontinuous splitting reaction can be carried out particularly advantageously according to the invention with multistage loop reactors, for example in two steps, that is, with two fat splitting steps or stages. In doing so, preferably about two thirds of the final splitting degree are already reached in the first step or stage in which the aqueous glycerol containing phase of the second stage is used as water phase. About one third of the desired splitting degree is achieved in the second step or stage which is supplied with fresh water as water phase. In this manner, splitting degrees of more than 90% can also be obtained without having to accept a remarkable longer reaction time. Both stages have their own enzyme recirculation that is discharged batch-wise and in intervals, as mentioned further above. Fresh enzyme is added to the circulated enzyme of each stage mainly in order to compensate for enzyme ageing. The enzyme losses caused by discharge with the aqueous and organic phases are, however, not important according to the invention.

The splitting process is particularly advantageous if all or two of the above stated three solution aspects according to the invention are combined. However, it has to be recognized that each of them alone also solves the object underlying the invention. The reaction time for a complete conversion could be shortened without further process optimization to a process period of only two hours and the consumption of enzyme could be reduced to 0.02 weight % of the oil charged into the process. This value could even be further lowered by using said additional polishing centrifugal separator.

The process according to the invention of the enzymatic fat/oil splitting is also, for the first time, superior in comparison to a large-scale high pressure splitting: The enzyme consumption costs lie well below the amortization costs for the considerable investment necessary for a pressure splitting plant, the enzyme splitting qualitatively provide more high grade products, the energy consumption is clearly lower and the process is technically unproblematic with regard to security. The products are especially high-graded as they exhibit, because of the low temperature, less by-products (decomposition products and undesired products generated in side reactions of the splitting reaction, as they occur with oils having non-saturated fatty acids). The material can be completely split and converted alone by means of the enzymatic splitting without having to be subjected to a further pressure splitting process.

According to the invention, it is preferred to use, as in the aforementioned publications, non-specific or mixtures of non-specific and specific lipases as enzymes. Suitable enzymes are indicated in the embodiments. Alternatively, the process according to the invention according to each of the solution aspects can be run only with specific enzymes, and it can thus produce e.g. monoglycerinoleate or other mono- or diglycerides. In this case, it is advantageous to maximize the monoglycerinoleate in the residue of the distillation, what is quite possible with the inventional features.

The process according to the invention according to each one of the above aspects is also suitable for splitting the mono-, di- and triglyceride that are contained in the so-called soap-stock from the alkali refining processes of edible oils. In this manner, the soap-stock can be quantitatively converted without prior saponification of the neutral oils into the fatty acids. For this purpose, the fatty acids being chemically bonded in the soaps are released, preferably before splitting, through an addition of acid. Preferably, a buffer solution is used in addition to water and enzyme for the splitting process. A possible solution is indicated in the preferred embodiments.

In technical experiments conducted by the inventors, a raw non-refined high-oleic sunflower oil was used. An advantage of the invention is that it is applicable to practically all oils and fats, among others, also to conventional sunflower oil with a normal content of oleic acid. Preferably, a buffer solution of soft water (free from materials that impede the enzyme reaction) and sodium acetate/acetic acid is used as aqueous phase. However, other buffers, such as sodium or potassium salts, carbonate, citrates or phosphates as well as the acids thereof, can be used in order to optimize the activity of the enzyme.

Figure 1:
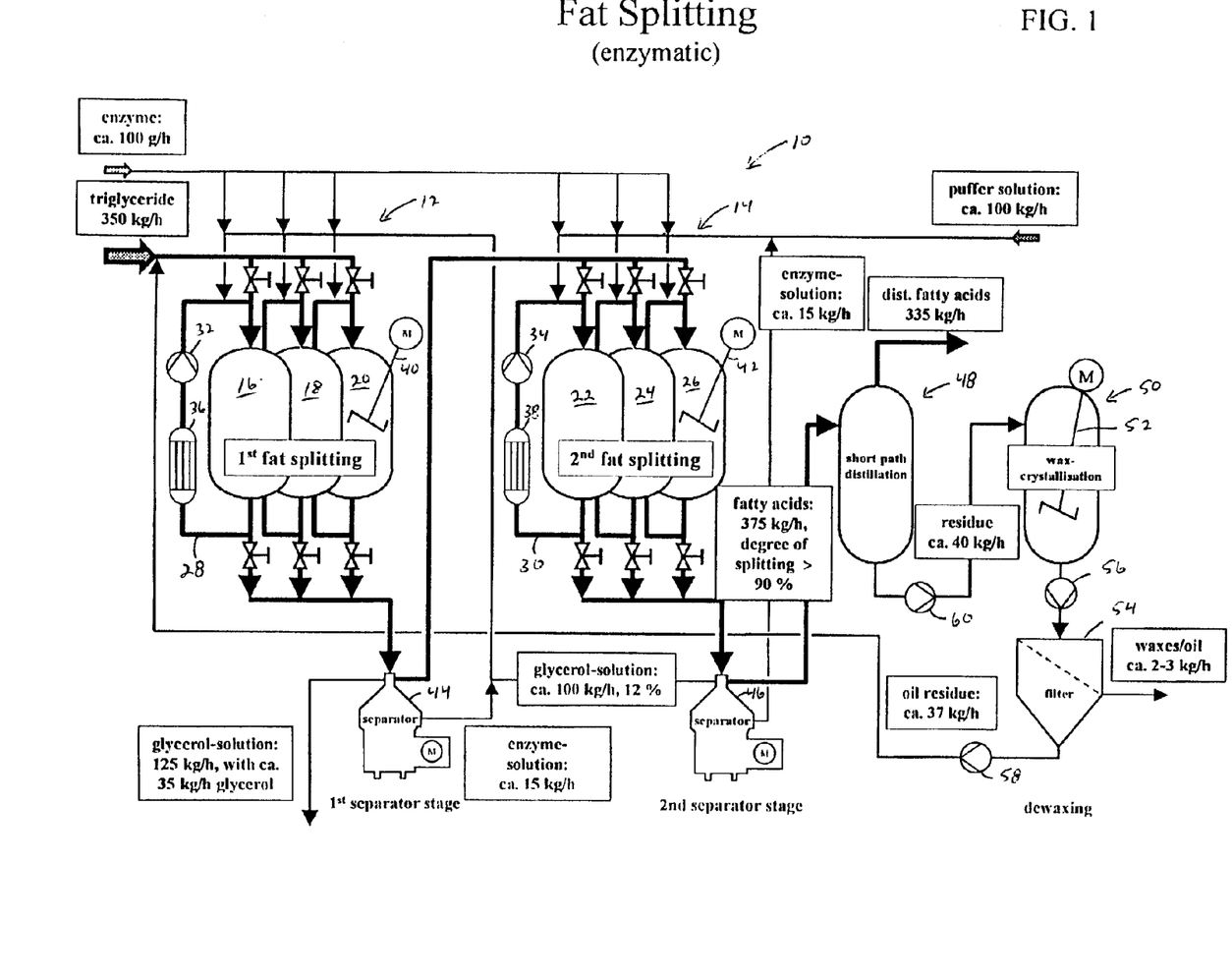
FIG. 1 shows a schematic drawing of an example for an industrial process showing an embodiments according to the invention.
Figure 2:
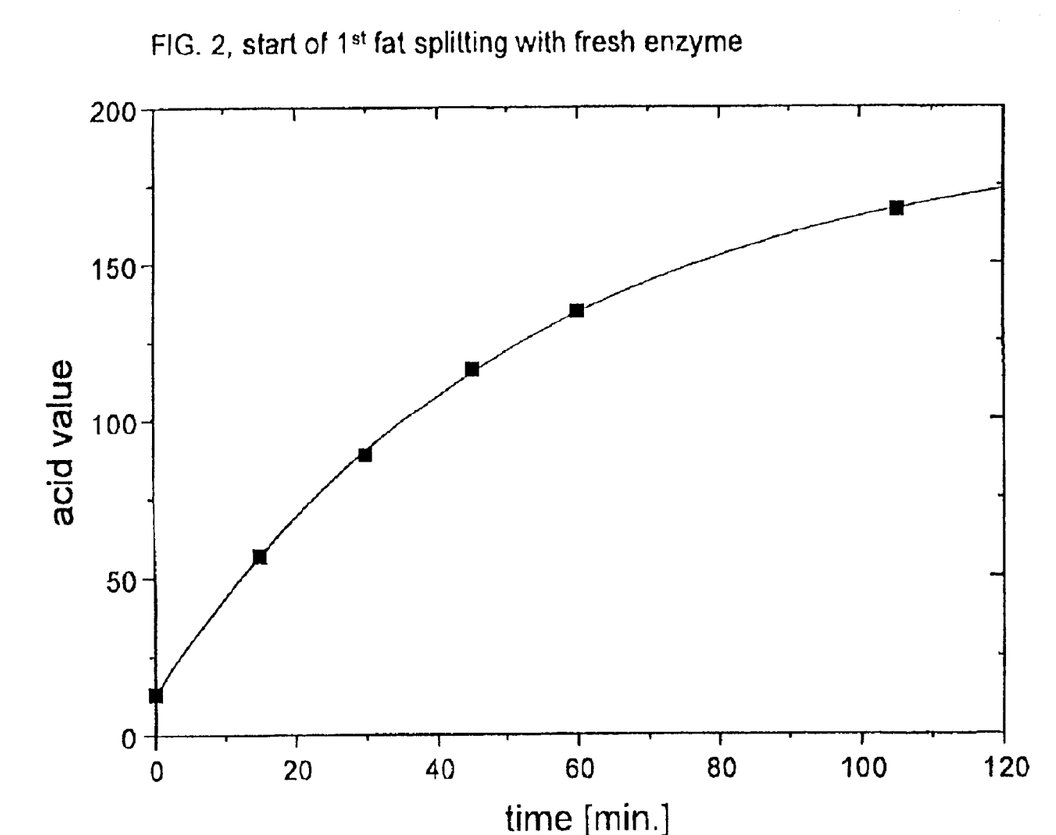
FIGS. 2 to 6 show increasing acid values of the converted oil that occur during different stages of the process.

FIG. 1 shows an arrangement of a two-stage fat-splitting apparatus 10 incorporating the present invention which is adapted to implement the explained aspects to provide throughput capacities for an industrial plant. Two fat-splitting steps or stages 12, 14 are provided that comprise in each case three loop reactors 16, 18, 20, 22, 24, 26 with a corresponding circulation loop 28, 30. The reactors 16, 18, 20, 22, 24, 26 are, as mentioned above, intermittently operated. Preferably, the circulation loop 28, 30 provided for each of the three reactors 16, 18, 20, 22, 24, 26 in a stage 12, 14 includes a centrifugal pump 32, 34 and a heat exchanger 3, 38 preceding the pump 32, 34. Most preferably, each reactors 16, 18, 20, 22, 24, 26 consist e.g. of glass or stainless steel containers with an agitator 40, 42. Moreover, a centrifugal separator 44, 46 is provided in the form of a self-cleaning centrifugal separator with disk stack for each stage 12, 14.

The outlet of the separator 46 of the second splitting stage 14, from where the organic phase with the fatty acids is discharged, is connected to a short path distillation means 48, in which, for example, a vacuum distillation for separating the free fatty acids is effected. The residue or bottom of the distillation is supplied, such as by a pump 60, to a crystalliser 50 comprising an agitator means 52, in which a wax crystallisation is achieved. The residual oil drawn form the wax crystallisation means 50 and carrying waxes and other high boiling by-products which have been crystallized out as solid matter, is introduced into a filter device 54 by means of a pump 56, and is freed from these by-products by filtering. Then the purified oil is conducted back to the first stage 12 of the splitting process apparatus 10 using a pump 58.

The reactors 16, 18, 20, 22, 24, 26 are fed with a buffer solution, the triglyceride to be split and enzyme. Moreover, enzyme solution is obtained in every intermittent bowl discharge of the self-cleaning centrifugal separators 44, 46 and returned into the reactor 16, 18, 20, 22, 24, 26 of the same stage 12, 14 that is to be filled and to which the respective discharged separator 44, 46 is connected at that time. Thus the enzyme, together with separated portions of free fatty acids concurrently discharged, triglycerides not yet split etc., remain in the circulation of the same stage or step. By this, it is prevented that starting products of different quality of the two stages 12, 14 underly back-mixing. The danger of back or reverse reactions is reduced in this way, too. Finally, it should be mentioned that an aqueous glycerol solution is drawn from the separator 44 of the first stage 12 as the separated heavier liquid phase and is thus provided for further processing. The aqueous glycerol solution drawn from separator 46 of the second stage 14 is fed back to the loop reactor of the first stage 12 being filled.

In the following examples, a process according to the invention with all three solution aspects is explained by means of the figures. In particular, FIGS. 2 to 6 clearly show that the slow-down of the splitting reaction varies such that the slow-down becomes greater with increasing reaction time.

EXAMPLE 1

In order to reach the operational phase, a starting phase must initially be run, which, as discussed above, does not yet meet the optimal limit values of the process according to the invention. In the Example 1 process, the starting phase includes a first fat splitting and a second fat splitting, both of which use fresh enzyme. The starting phase is followed by the operational phase which includes a first fat splitting and a second fat splitting, both of which use recovered enzyme. Following the operational phase, the raw fatty acid is processed through a short path distillation and the oil residue is recovered for reuse.

In the first fat splitting of the starting phase, a reactor of the first stage is charged with 30.0 kg of raw, non-refined high-oleic sunflower oil 90 plus (Registered Trademark) of the company Dr. Frische GmbH, with an acid value of 4 (ascertained by titration against potassium hydroxide solution according to DIN 53169 and DIN 53402), together with 7.0 kg of a buffer solution that consists of a glycerine/water solution with 12% by weight glycerol and that is buffered with 3.0 g sodium acetate. The charged mixture of oil and buffer solution is supplied to a reactor of the first stage and circulated under agitating by means of a centrifugal pump and heated to 35–40° C. After that, 30 g of an enzyme of "candida rugosa" OF 360 (a lipase in form of a powdered solid matter from Meito Sangyo, Japan, 360,000 U/g (units/ g) are added.

The splitting process is monitored by measuring the acid value. After 50 minutes the acid number determined as above by titration, according to FIG. 2, amounts to 135, corresponding to a splitting degree of 68%. The splitting degree results from the acid value (135 in the present case) measured by titration and divided by the theoretic acid value (around 199) which is calculated for the mixture of free fatty acids and side substances or by-products, which is to be expected for the charged oil in the process. The mixture is now no longer stirred and no longer circulated. Around 5 minutes after both, the agitator and the circulation pump, have been switched off, the stabilized mixture is subjected to centrifugal separation in the centrifugal separator of the first stage (a self-cleaning disk stack centrifuge SA1-01 of the company Westfalia Separator AG) to obtain as separated phases an organic, fatty acid containing phase and an aqueous glycerol phase. During this separation process approx. 40 kg/h of reactor content flow through the centrifugal separator and the bowl of the separator is completely hydraulically discharged every 15 minutes.

Approx. 2 kg of emulsion layer enriched with enzyme are obtained as bowl discharge product. The discharge product contains the enzyme, which has been enriched in the emulsion layer between the organic phase and the aqueous phase, and is supplied to the reactor of the first stage which is about to be filled or charged with oil, water, enzyme and buffer solution. The aqueous phase is enriched with glycerol generated by splitting up to about 36% by weight. The liquid organic phase with free oleic acids is almost free of aqueous phase and only contains small residual quantities of enzyme. The acid value of the organic phase is 142 due to a further splitting taking place during the phase separation when discharging and processing the reactor container via the centrifugal separator.

Figure 3:
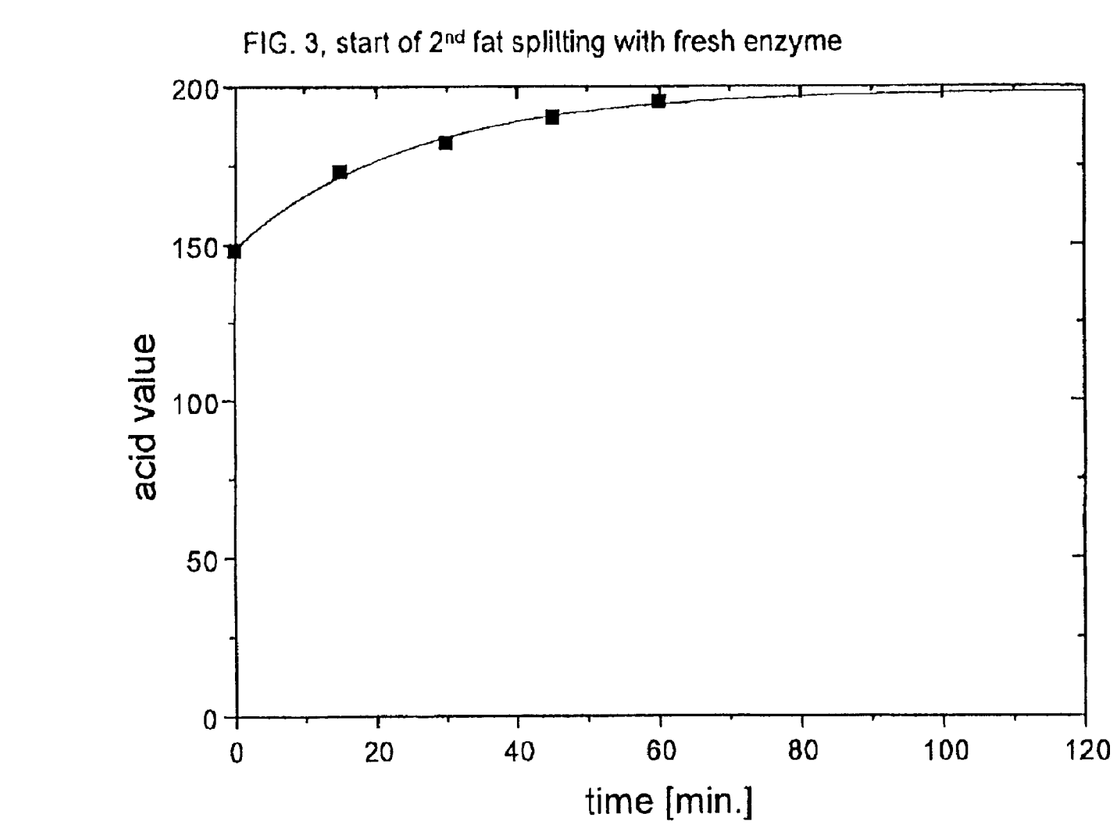
Figure 4:
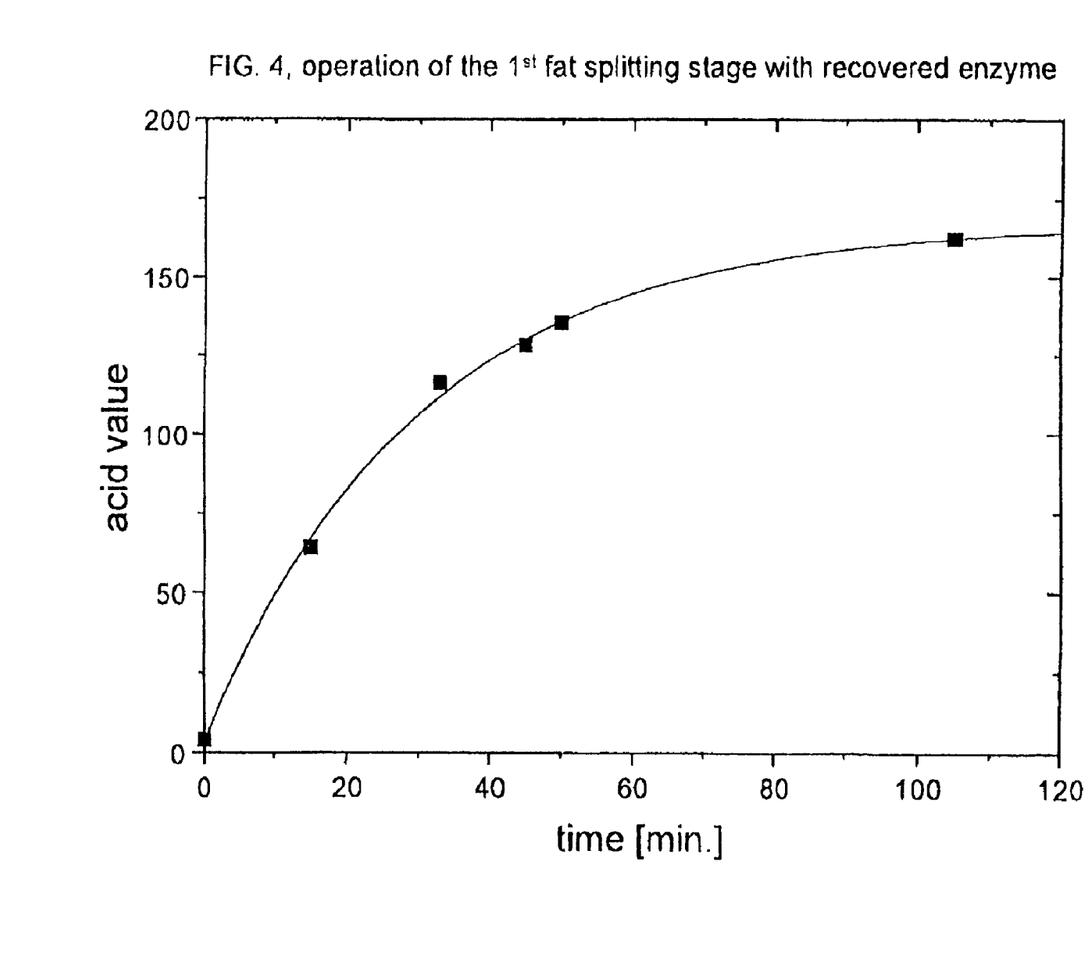
Figure 5:
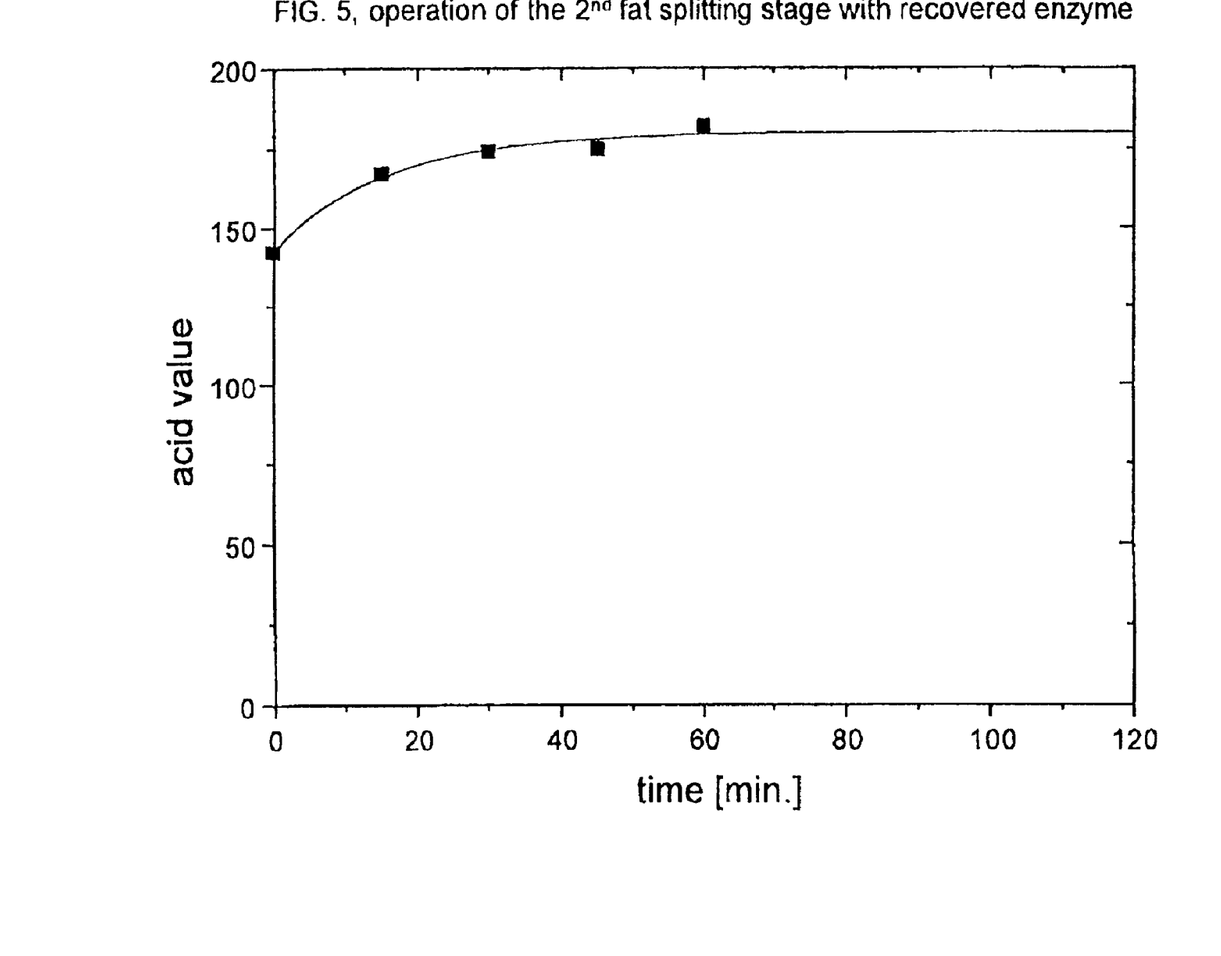
Figure 6:
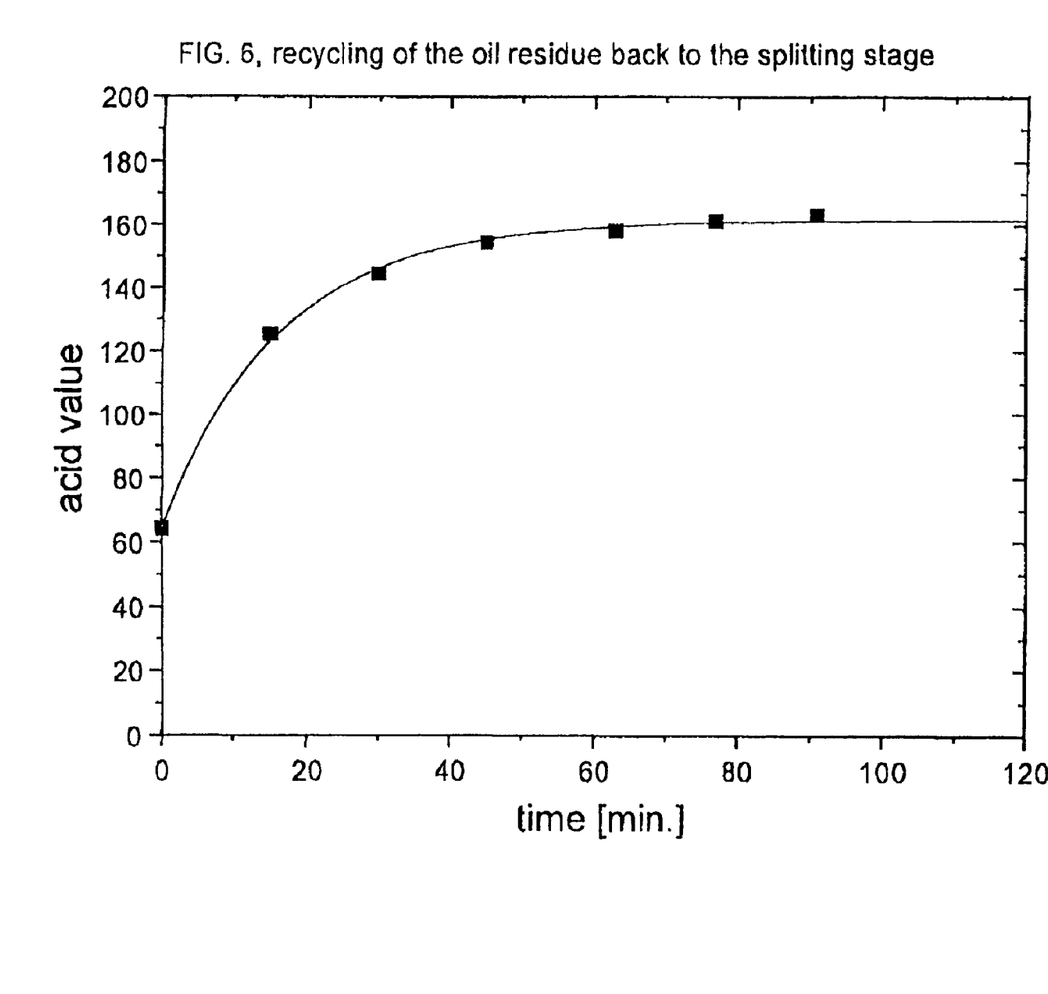

In the second fat splitting of the starting phase, the organic phase containing oleic acid of the first step or stage is supplied to the reactor of the second fat-splitting stage, which is about to be filled, and, now after mixing at the end of a post-reaction, has an acid value of 148 (FIG. 3). The same reactor is fed with 7.0 kg of a buffered solution freshly prepared from soft water and 3 g of sodium acetate and 30 g of the aforementioned lipase.

After 60 minutes, the acid value is above 190, corresponding to a splitting degree of more than 95%. The mixture is now no longer stirred and no longer circulated and separated by means of the separator of the second stage under the same conditions as in case of the first stage. A clear organic phase enriched with oleic acid flow off from the side of the lighter phase of the separator during this separation step. This drawn off organic phase is subjected to a short path distillation.

A glycerol in water/buffer solution with 12% by weight of glycerol flows off from the centrifugal separator as heavy phase and is returned into the reactor of the first stage, which is about to be filled. About 2 kg emulsion phase enriched with enzyme result as bowl discharge product. This is supplied to the reactor being about to be filled of the second stage.

In the first fat splitting of the operational phase, a reactor to be filled of the first step is charged with 30.0 kg of the aforementioned oil together with the 12% by weight glycerol in water/buffer solution of the second separator stage (here still from the starting phase). This mixture is circulated by agitating by means of a centrifugal pump and heated to 35–40° C. After that, the 2 kg bowl discharge product of the first separator stage of the 'start experiment' which corresponds to the emulsion enriched with enzyme and 3 g of fresh lipase of the aforementioned type are also added.

After 60 min., the acid value is 134 (FIG. 4), corresponding to a splitting degree of around 68%. Now the mixture is separated as in the starting phase, and, on the side of the heavy phase, a glycerol in water solution with around 36% by weight of glycerol flows off and is taken out of the process.

In the second fat splitting of the operational phase, the reactor of the second stage to be fed obtains the organic phase of the first stage, containing oleic acid. This phase has, after mixing the reactor content, an acid value of 142. Moreover, the reactor is fed with 7.0 kg of the above buffer solution as well as with the 2 kg bowl discharge product of the second separator stage of the 'start experiment', that is, the emulsion enriched with enzyme, and with 5 g of fresh lipase of the aforementioned type for refreshing.

After 60 minutes, the acid value is 184 (FIG. 5), corresponding to a splitting degree of 93%. The discharge of the reaction products is effected as in the starting phase, the clear organic phase enriched with oleic acid which is flowing off exhibiting an acid value of 185. A 12% by weight glycerol-water/buffer solution is separated and flows off from the separator. Around 2 kg of emulsion enriched with enzyme is obtained by bowl discharge.

The raw fatty acid obtained in such a manner in the second stage (acid number 184) is collected in a 200 liter barrel serving as intermediate container and is subjected to a short path distillation in a vacuum short path distillation device of the type KD 10 of the company UIC, Alzenau-Hörstein, with a preceding degasification stage for separating possible small quantities of moisture. For example, the distillation is carried out with a total pressure of 0.014 mbar and at 191° C. Then around 8% by weight of the fatty acids having been supplied continuously are discharged at the bottom of the distillation means as residue not boiling under these conditions. The remaining 92% by weight of the crude product distill as oleic acid with an acid number of 199–200 and only smallest quantities of by-products in form of fatty acids with lower vapour pressure. This value corresponds, within the range of measuring precision, to the theoretically calculated acid number. (The value is, due to a small portion of more easily volatile fatty acids of shorter chain-length, slightly higher than the theoretic acid value).

The residual product is subjected to dewaxing and, thereby, the present higher fatty acids (C22 and longer chain lengths), waxes and other higher-boiling by-products of the oil crystallize as solid matters and are separated by means of filtration.

The reuse of the oil residue was performed as aliquot on laboratory scale in order to demonstrate this process advantage. This was also justified, since the preliminary tests had shown that conditions being very well comparable to the enzymatically catalysed conversion of oil with water can be adjusted in laboratory scale.

In a 500 ml round-bottom flask used to recover the oil residue, 91.5 g of the filtered residual product together with 91.5 g of raw, non-refined High-Oleic sunflower oil 90 plus of Dr. Frische GmbH, and 46.0 g of said buffered 12% by weight glycerol-in-water solution of the second separator stage are prepared and mixed with a magnet stirrer at 1000 rev./min. The acid value of the mixture amounts to 64. While doing that, the reaction mixture is heated to around 40° C. on a water bath. After the reaction mixture has been heated to 40° C., an amount of 0.19 g of lipase of the aforementioned type being an adequate quantity to the aforementioned test is added and the reaction is monitored by means of the acid value (see FIG. 6). The course of the acid values shows that recycling of the oil residue improves the process regarding efficiency.

In the present embodiment the temperature in the splitting reactor was kept at 35 to 40 ° C. The process according to the invention can, however, in general, be carried out between around 20 ° C. and 90° C. The lower limit is determined by the flowability of the liquid to be mixed, whereas the upper limit is determined by the thermal stability of the enzyme and by the lowest boiling temperature in the liquid mixture.

The number of the splitting stages can be increased, e.g. already with three steps the glycerol concentration can be noticeably increased. As already mentioned, according to the second and third solution aspect of the present invention, already after a short time noteworthy high splitting degrees can be achieved, which, as the start phase of the test experiment shows, can reach over 95%. In this respect, however, the procedural approach according to the first aspect is more difficult.

The splitting degree achieved in the only, or in the last, splitting reactor can be varied in wide limits. Recommendable are values not below 80% and the preferred values are over 90%, in order to be able to fully exploit the process capacities. In case of special applications with specific enzymes one could also work with a splitting degree as low as 60%.

The enzymatic fat splitting according to the invention has also successfully been applied on fatty acid ethyl esters. In general, enzymatically splittable esters can be split with advantage according to the second and third aspect of the invention. The possibility of applying the process according to the first solution aspect depends on the alcohol and fatty acid components being generated in the process.

EXAMPLE 2

A further embodiment was carried out as outlined under the starting and operational phase, however, using 60 g of the above enzyme OF 360 in the starting phase. Only after 30 minutes residence time within two splitting stages, a splitting degree corresponding to the degree achieved after 60 minutes in example 1 could be achieved in this embodiment.

EXAMPLE 3

A further embodiment was carried out as outlined under the starting and operational phase of Example 1 which uses 60 g OF 360 in the starting phase as enzyme and tallow (bft: bleachable, fancy tallow) as fat instead of the oil. The tallow had a quality which corresponds to the quality of tallow which is commonly subjected to high pressure hydrolysis in conventional pressure fat splitting plants. Again, the same high splitting degree of about 93% could be reached only after 30 minutes as in case of high-oleic sunflower oil.

EXAMPLE 4

A further embodiment was carried out as outlined under the starting and operational phase of Example 1 using a mixture (1500 g) of the above unspecific enzyme OF 360 (60 g) and an enzyme Novozym 388 (1440 g in liquid form, 20 000 U/g, of Novozymes A/S, Denmark) which is able to specifically split long-chain fatty acids chemically bonded to the 1, 3 position on the triglyceride backbone, in the starting phase. In other words, Novozym 388 has good positional specificity for the 1, 3 position and poor positional specificity for the 2 position whereas OF 360 as typical unspecific enzyme only very slowly splits the ester bonds at the 1, 3 position. Furthermore, 30 kg of crambe oil having 60% erucic acid was subjected to instead of sunflower oil. A splitting degree of 80% could be achieved using the same conditions as in the starting phase of Example 1. Likewise, the raw fatty oil can be subjected to short path distillation and the oil residue recovered, such as described in Example 1 can be successively applied to this example. This result was due to the fact that Novozym 388 has good positional specificity for the 1, 3 position which is mainly occupied in case of erucic acid and that b. the unspecific enzyme OF 360 was also present. Using the 1,3 specific enzyme and the unspecific enzyme alone did not reveal comparable good results.

While there has been shown and described what are at present considered the preferred embodiments of the invention, it will be obvious to those skilled in the art that various changes and modifications can be made therein without departing from the scope of the invention defined by the appended claims.

We claim:

1. A method of enzymatically splitting triglycerides for obtaining fatty acids and glycerol utilizing at least one lipase acting as a biocatalyst, wherein the method comprises:

preparing a mixture which contains triglycerides, water and at least one lipase;

subjecting the mixture to a glyceride splitting process to create a reaction mixture;

subjecting the reaction mixture to a centrifugal separation step for separating an aqueous, glycerol-containing phase obtained in the glyceride splitting process from an organic phase, which contains split free fatty acids, by supplying the reaction mixture into a self-cleaning centrifugal separator, said self-cleaning centrifugal separator allowing continuous discharge of the aqueous and organic phases and an intermittent bowl content discharge;

adjusting said self-cleaning centrifugal separator such that an interfacial emulsion-like layer developing between said aqueous and organic phase accumulates within the self-cleaning centrifugal separator, said interfacial emulsion-like layer having a lipase content that is greater than the lipase content in either of the aqueous and organic phases;

continuously discharging the aqueous, glycerol-containing phase and the organic phase from the self-cleaning centrifugal separator as the interfacial emulsion-like layer accumulates within the self-cleaning centrifugal separator;

subjecting the self-cleaning centrifugal separator to a bowl discharge after predetermined time periods to discharge bowl content containing a major portion of the interfacial emulsion-like layer accumulating within the self-cleaning centrifugal separator; and feeding back at least a portion of the discharged bowl content of the self-cleaning centrifugal separator into the glyceride splitting process.

2. The method according to claim 1, wherein said at least one lipases is selected from the group consisting of non-specific lipases, specific lipases, and a mixture of non-specific and specific lipases.

3. The method according to claim 1, wherein the organic phase residue that remains after the separation of the fatty acids from the obtained organic phase is dewaxed and afterwards returned into the glyceride splitting process.

4. The method according to claim 1, wherein the organic phase leaving the self-cleaning centrifugal separator is supplied to a polishing centrifugal separator, which is also subjected to an intermittent bowl discharge, in order to recover any residual lipase separated in the form of a deposit on the bowl wall for returning said residual lipase into the glyceride splitting process.

5. The method according to claim 1 in which said mixture includes mono-, di- and triglycerides of soap stocks.

6. The method according to claim 1, wherein the glyceride splitting process is carried out in a first stage and a second stage, in said first stage the mixture is split a first predetermined amount to form a first aqueous glycerol phase and a first organic phase, and said second stage is split a second predetermined amount to form a second aqueous glycerol phase and a second organic phase, wherein the second aqueous glycerol phase obtained from the second stage is supplied to the first stage as a water phase and that the second stage is supplied with fresh water as a water phase and the first organic phase obtained in the first stage.

7. The method according to claim 1, wherein said interfacial emulsion-like layer developing between said aqueous and organic phase accumulates within a disk stack of the self-cleaning centrifugal separator.

8. The method according to claim 1, wherein said glyceride splitting process comprises:

subjecting the mixture to a glyceride splitting reaction until reaching a splitting degree at which, for said mixture, the slow-down of the splitting reaction is below a preset value;

separating the fatty acids to be obtained from the mixture of the glyceride splitting process, which comprises an aqueous, glycerol containing phase and a partially split organic phase containing split free fatty acids, by first separating said aqueous phase from said partially split organic phase containing the split free fatty acids in said self cleaning centrifugal separator, and thereafter, separating the free fatty acids from the separated partially split organic phase; and feeding back the obtained residue of the organic phase freed from the free fatty acids into the glyceride splitting process.

9. The method according to claim 8, wherein the splitting reaction is carried out only until a splitting degree between 60 and 95% is reached, and for separating the free fatty acids, the separated partially split organic phase is subjected to a vacuum distillation being selected from a short path distillation and a falling-film distillation.

10. The method according to claim 1, wherein said glyceride splitting process is carried using a plurality of parallel splitting loop reactors, each of the splitting loop reactors having a circulation loop, and said glyceride splitting process including supplying said mixture into a first one of said reactors of said plurality of parallel splitting loop reactors wherein the circulation loop of said first one of said reactors is not activated while the first one of said reactors is being filled, and at the same time, operating a second one of said reactors of said plurality of parallel splitting loop reactors of the same stage with an active circulation loop in a splitting operational mode, and at the same time, operating a third one of said reactors of said plurality of parallel splitting loop reactors of the same stage such that the circulation loop thereof is not active and the reactor content of said third one of said reactors is discharged into said self-cleaning centrifugal separator.

11. The method according to claim 10, wherein the second one of said reactors is operated such that the mixture is subjected to a glyceride splitting reaction until reaching a splitting degree at which, for said mixture, the slow-down of the splitting reaction rate is below a preset value, and wherein the separation step behind the third one of said reactors comprises separating the fatty acids to be obtained from the mixture of the glyceride splitting process, which comprises an aqueous, glycerol containing phase and a partially split organic phase containing split free fatty acids, by first separating said aqueous phase from said partially split organic phase containing the split free fatty acids in said self-cleaning centrifugal separator, and thereafter, separating the free fatty acids from the separated partially split organic phase, and feeding back the obtained residue of the organic phase freed from the free fatty acids into the glyceride splitting process.

12. The method according to claim 1, wherein the residue of the organic phase, after having been subjected to a dewaxing step, is mixed with a fresh mixture to be split containing triglycerides, water and lipase.

* * * * *